(12) United States Patent
Dudzinski et al.

(10) Patent No.: US 12,171,418 B2
(45) Date of Patent: Dec. 24, 2024

(54) TRANSCATHETER ATRIAL SEPTAL CLOSURE DEVICE

(71) Applicant: TAVR SOLUTIONS, LLC, St. Louis, MO (US)

(72) Inventors: David Dudzinski, St. Louis, MO (US); Spencer Toder, St. Louis, MO (US)

(73) Assignee: TAVR SOLUTIONS, LLC, St. Louis, MO (US)

( * ) Notice: Subject to any disclaimer, the term of this patent is extended or adjusted under 35 U.S.C. 154(b) by 44 days.

(21) Appl. No.: 17/945,536

(22) Filed: Sep. 15, 2022

(65) Prior Publication Data

US 2023/0085611 A1 Mar. 16, 2023

Related U.S. Application Data

(60) Provisional application No. 63/244,746, filed on Sep. 16, 2021.

(51) Int. Cl.
*A61B 17/00* (2006.01)
(52) U.S. Cl.
CPC .............. *A61B 17/0057* (2013.01); *A61B 2017/00575* (2013.01); *A61F 2210/0014* (2013.01)
(58) Field of Classification Search
CPC ...... A61B 17/0057; A61B 2017/00575; A61B 2017/00579; A61B 2017/00584; A61B 2017/00592; A61B 2017/00597; A61B 2017/00601; A61B 2017/00606; A61B 2017/0061; A61B 2017/00615; A61B 2017/00623; A61B 2017/00628;

(Continued)

(56) References Cited

U.S. PATENT DOCUMENTS

| | | |
|---|---|---|
| 4,917,089 A | 4/1990 | Sideris |
| 5,108,420 A | 4/1992 | Marks |
| 5,171,259 A | 12/1992 | Inoue |

(Continued)

FOREIGN PATENT DOCUMENTS

EP 1417933 A1 12/2004

OTHER PUBLICATIONS

International Search Report for Corresponding Application Serial No. PCT/US2022/043638, Dated Dec. 23, 2022, pp. 1-8.

(Continued)

*Primary Examiner* — Dianne Dornbusch
(74) *Attorney, Agent, or Firm* — Tarolli, Sundheim, Covell & Tummino LLP

(57) ABSTRACT

A closure device for sealing an atrial septal defect is provided. The closure device includes a distal closure portion and a proximal closure portion. The distal closure portion includes a distal membrane covering a plurality of distal fingers that extend in a distal plane. The proximal closure portion includes a proximal membrane covering a plurality of proximal fingers that extend in a proximal plane. The closure device also includes a waist section extending axially between the plurality of distal fingers and the plurality of proximal fingers. The distal closure portion is configured to sealingly engage one of the left or right side of a septal wall, the proximal closure portion is configured to sealingly engage the other of the left or right side of the septal wall, and the waist section is configured to be positioned and centered in an atrial septal defect between the left and the right septal wall.

14 Claims, 18 Drawing Sheets

(58) Field of Classification Search
CPC .......... A61B 2017/00632; A61B 2017/00637; A61B 2017/00641; A61F 2210/0014
See application file for complete search history.

(56) References Cited

U.S. PATENT DOCUMENTS

| | | | |
|---|---|---|---|
| 5,334,217 A | 8/1994 | Das | |
| 5,846,261 A | 12/1998 | Kotula et al. | |
| 5,976,174 A | 11/1999 | Ruiz | |
| 6,171,329 B1 | 1/2001 | Shaw et al. | |
| 6,221,092 B1 | 4/2001 | Koike et al. | |
| 6,440,152 B1 * | 8/2002 | Gainor | A61B 17/0057 606/213 |
| 6,712,836 B1 * | 3/2004 | Berg | A61B 17/0057 606/213 |
| 7,144,410 B2 | 12/2006 | Marino et al. | |
| 9,216,014 B2 | 12/2015 | Devellian et al. | |
| 9,474,517 B2 | 10/2016 | Amin et al. | |
| 9,681,948 B2 | 6/2017 | Levi et al. | |
| 10,265,059 B2 | 4/2019 | Rowe et al. | |
| 10,278,705 B2 | 5/2019 | Amin et al. | |
| 10,357,357 B2 | 7/2019 | Levi et al. | |
| 10,632,292 B2 | 4/2020 | Forcucci et al. | |
| 11,253,353 B2 | 2/2022 | Levi et al. | |
| 11,259,789 B2 | 3/2022 | Rowe et al. | |
| 11,426,172 B2 | 8/2022 | Melanson et al. | |
| 2009/0076541 A1 | 3/2009 | Chin et al. | |
| 2013/0016596 A1 | 6/2013 | Amin et al. | |
| 2014/0031862 A1 | 1/2014 | Chanduszko | |
| 2014/0358180 A1 | 12/2014 | Malakan Rad et al. | |
| 2014/0379020 A1 | 12/2014 | Campbell et al. | |
| 2015/0142049 A1 * | 5/2015 | Delgado | A61B 17/3468 606/216 |
| 2015/0313599 A1 * | 11/2015 | Johnson | A61B 17/0057 606/191 |
| 2016/0022970 A1 | 1/2016 | Forcucci et al. | |
| 2017/0367710 A1 | 12/2017 | Yang | |
| 2018/0256865 A1 * | 9/2018 | Finch | A61M 27/002 |
| 2018/0333150 A1 * | 11/2018 | Bak-Boychuk | A61B 17/0057 |
| 2022/0168098 A1 | 6/2022 | Levi et al. | |
| 2022/0175364 A1 | 6/2022 | Rowe et al. | |
| 2022/0313234 A1 | 10/2022 | McNamara et al. | |

OTHER PUBLICATIONS

Hopkins RA, Bert AA, Buchholz B, Guarino K, Meyers M. Surgical patch closure of atrial septal defects. Ann Thorac Surg. Jun. 2004;77(6):2144-9; author reply 2149-50. doi: 10.1016/j.athoracsur.2003.10.105. PMID: 15172284.

* cited by examiner

TRANSCATHETER ATRIAL SEPTAL CLOSURE DEVICE

CROSS-REFERENCE TO RELATED APPLICATIONS

The present application claims priority to U.S. Provisional Application No. 63/244,746 filed on Sep. 16, 2021.

TECHNICAL FIELD

The present disclosure relates to an occlusion or closure device to seal an atrial septal defect.

BACKGROUND

The heart has two sides separated by two inner dividing walls, or septa, which are known as the interatrial septum and the interventricular septum. The right side of the heart receives oxygen-poor blood from the body and pumps it into the lungs, where it is oxygenated. The left side of the heart receives the oxygen-rich blood from the lungs and pumps it to the body. The interatrial septum separates the upper chambers of the heart, and the interventricular septum separates the bottom chambers of the heart. Each septum serves to prevent the mixing of blood between the right and left sides of the heart.

Apertures, or holes, in the septa of the heart are defects that can affect the normal flow of blood through the heart. Such apertures can occur congenitally or be caused by medical procedures including puncturing by a medical device or the like. An aperture in the interatrial septum between the heart's two upper chambers is known as an atrial septal defect ("ASD"), with secundum ASDs being the most common form of ASDs. An ASD can cause the mixing of oxygen-rich blood with oxygen-poor blood. Such mixing of blood with differing oxygen contents can cause blood with high oxygen content to be pumped to the lungs rather than the body, and blood with low oxygen content to be pumped to the body rather than the lungs, which is known as blood shunting. Depending upon the size of the aperture and the amount of blood shunting, this can result in a spectrum of diseases including, without limitation, abnormal heart rhythms, abnormal elevation in blood pressure in the pulmonary arteries, and congestive heart failure, embolic phenomena and strokes.

Over the past few decades, minimally invasive treatment techniques have been developed, and transcatheter treatment techniques have become preferred techniques for treating ASDs and avoiding the adverse side effects common to other treatment techniques. Specifically, percutaneous transcatheter treatment techniques provide for a safer and less invasive medical procedure. However, occlusion or closure devices used in known percutaneous transcatheter treatment techniques are not without their disadvantages. A number of transcatheter occlusion or closure devices generally employ umbrella-like structures to occlude or close ASDs. Known occlusion or closure devices have a number of specific disadvantages, including, but not limited to, a propensity to tear or fracture, a propensity to perforate body tissue, including heart tissue, a propensity for residual leaking, an elevated risk of complications due to thrombus, a tendency to erode the atrial and aortic walls, migration and other drawbacks. Further, many known occlusion or closure devices have high profiles and include large masses of foreign material, such as nitinol, an excess amount of occlusion or closure membrane or fabric, that may impair the adaptation of the device by the patient's body.

Another disadvantage of known occlusion or closure devices is that, in cases where the patient may need a subsequent transseptal procedure, the presence of the deployed or implanted device generally inhibits the ability to transseptally puncture the device for purposes of recrossing the septum or permitting interatrial re-entry. This disadvantage results from the fact that the structure of the deployed or implanted device may block the passage of certain-sized sheathes or other medical instruments through the septum and/or comprises materials that are incapable of permitting single or repeated transseptal punctures or interatrial re-entry therethrough. Further, after such occlusion devices are punctured, they cannot be re-sealed.

Another disadvantage of known occlusion or closure devices is their limited ability, or complete inability, to occlude or close holes or apertures that are located relatively low in a heart or its septum, because of the potential interaction or interference of such occlusion or closure devices with the tricuspid or mitral valves.

SUMMARY

The present disclosure relates to a device for closing an opening in a bodily tissue wall (also referred to herein as a "closure device"). The device can be used to treat abnormal openings, either man-made, congenital, or acquired, for example. In an aspect, a closure device is provided that comprises a continuous unitary frame. The frame has a plurality of radially extendible distal fingers extending in a distal plane, a plurality of radially extendible proximal fingers extending in a proximal plane. The proximal plane extends in a direction different than the distal plane. The frame further includes a waist section extending axially between the plurality of distal fingers and the plurality of proximal fingers. The closure device also includes a distal membrane covering at least one side of the plurality of distal fingers and a proximal membrane covering at least one side of the plurality of proximal fingers. The closure device is expandable from a radially collapsed configuration in which the frame is elongated axially to a radially expanded configuration in which the frame is shortened axially. In the radially expanded configuration, the waist section is configured to be positioned within the opening in the tissue wall, the plurality of distal fingers is configured to engage one side of the tissue wall defining the opening, and the plurality of proximal fingers is configured to engage the other side of the tissue wall defining the opening such that the distal and proximal membranes are pressed against the sides of the tissue wall to seal the opening. The closure device has a reduced propensity for tearing or rupturing, permits transseptal punctures or interatrial re-entry, and is configured to not interact or interfere with adjacent tissue, such as the aorta, tricuspid or mitral valves of the heart or other adjacent tissue where it would be undesirable to have such interference or interaction. Further, the closure device has very little amount of metal, which makes the device more malleable.

DETAILED DESCRIPTION

The present disclosure relates to medical devices for occluding or closing an opening in body tissue, including congenital heart defects. Such medical devices include collapsible and deployable atrial septal occlusion or closure devices that can be delivered through a catheter or sheath.

As used herein with respect to a described element, the terms "a," "an," and "the" include at least one or more of the described element(s) including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. The terms "first," "second," etc. are used to distinguish one element from another and not used in a quantitative sense unless indicated otherwise. By "integral" or "integrated" is meant that the described components are fabricated as one piece or multiple pieces affixed during manufacturing or the described components are otherwise not separable using a normal amount of force without damaging the integrity (i.e. tearing) of either of the components. A normal amount of force is the amount of force a user would use to remove a component meant to be separated from another component without damaging either component. As used herein a "patient" includes a mammal such as a human being. All closure devices as described herein are used for medical purposes and are therefore sterile. Although the drawings show certain elements of a closure device in combination, it should be noted that such elements can be included in other embodiments or aspects illustrated in other drawings or otherwise described in the specification. In other words, each of the disclosed aspects and embodiments of the present disclosure may be considered individually or in combination with other aspects and embodiments of the disclosure including patent applications incorporated by reference herein.

Figure 1:
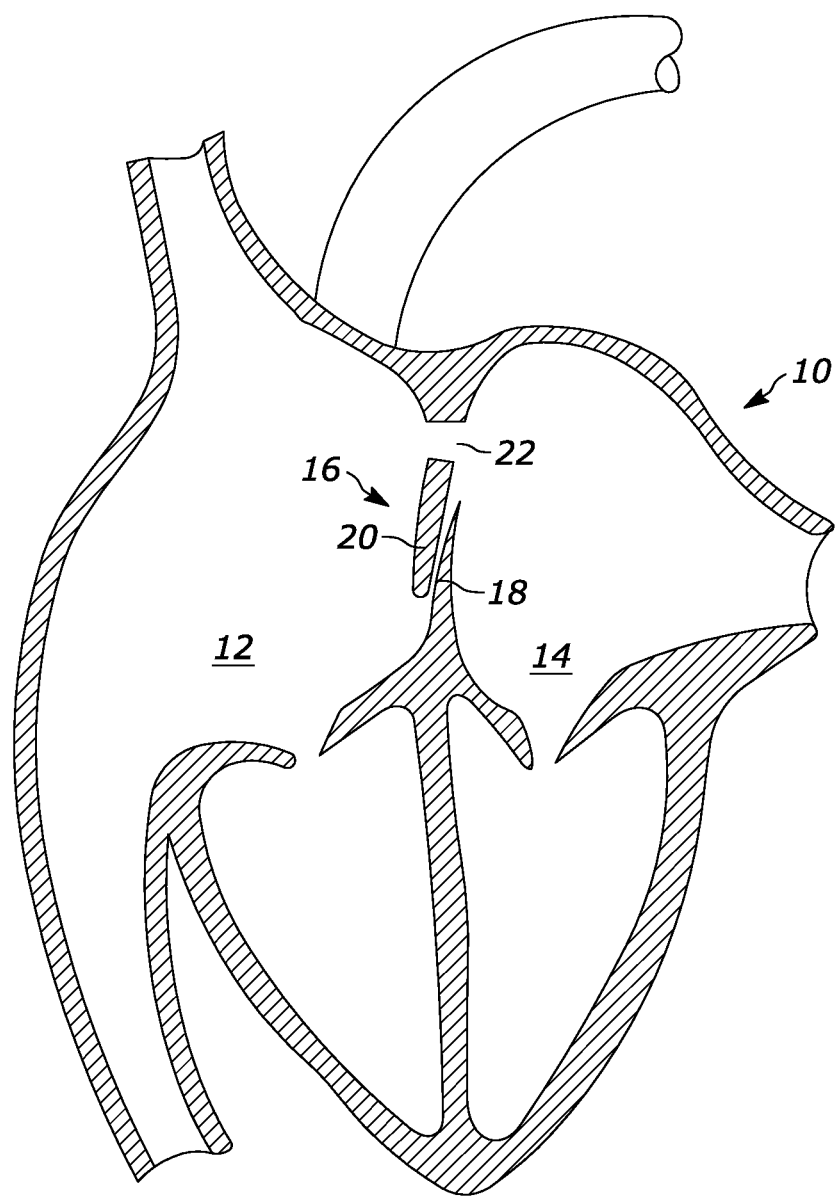
FIG. 1 is a schematic illustration of a human heart including an ASD.

FIG. 1 illustrates a human heart 10, having a right atrium 12, a left atrium 14, an atrial septum 16, and a septal aperture 22. The atrial septum 16 generally comprising a septum primum 18 and septum secundum 20. The anatomy of the septum 16 can vary widely within a population. For example, in some people, the septum primum 18 may be quite thin. As used herein, "left" refers to the left chambers of the heart 10, including the left atrium 14 and left ventricle, and "right" refers to the right chambers of the heart 10, including the right atrium 12 and right ventricle.

Figure 2:
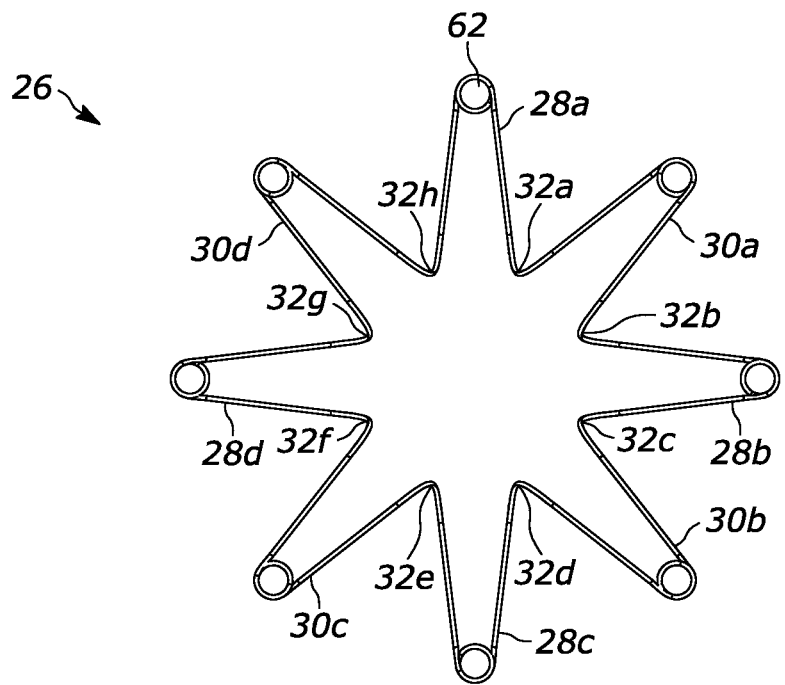
FIG. 2 is a top view of a frame of a closure device according to an aspect of the present disclosure.
Figure 3:
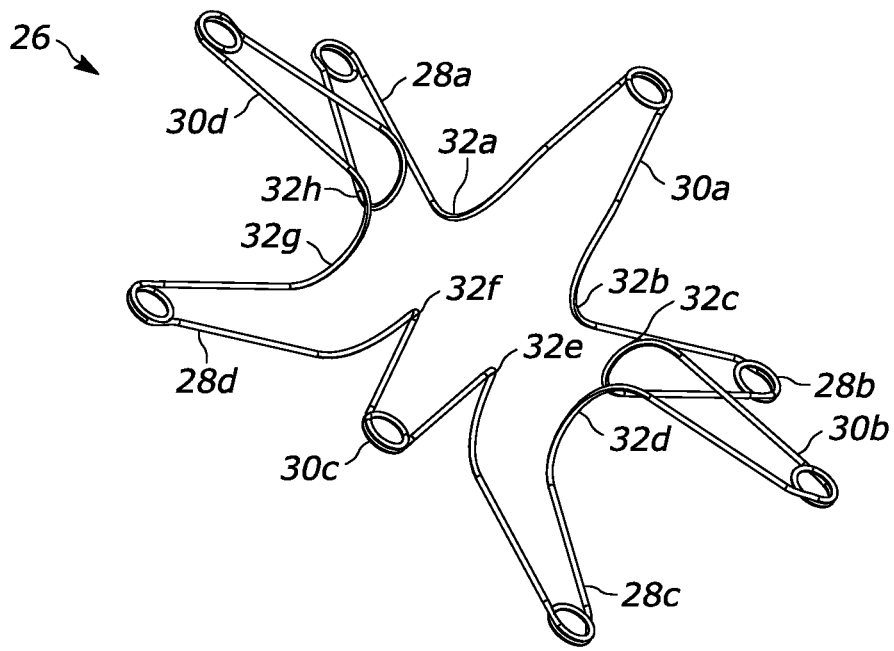
FIG. 3 is a perspective view of the frame of FIG. 2.
Figure 4:
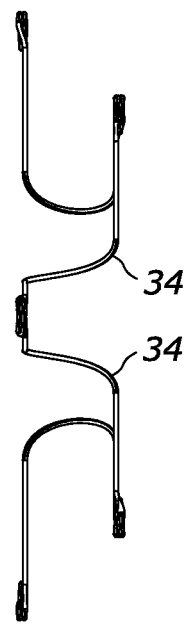
FIG. 4 is a side view of the frame of FIG. 2.
Figure 5:
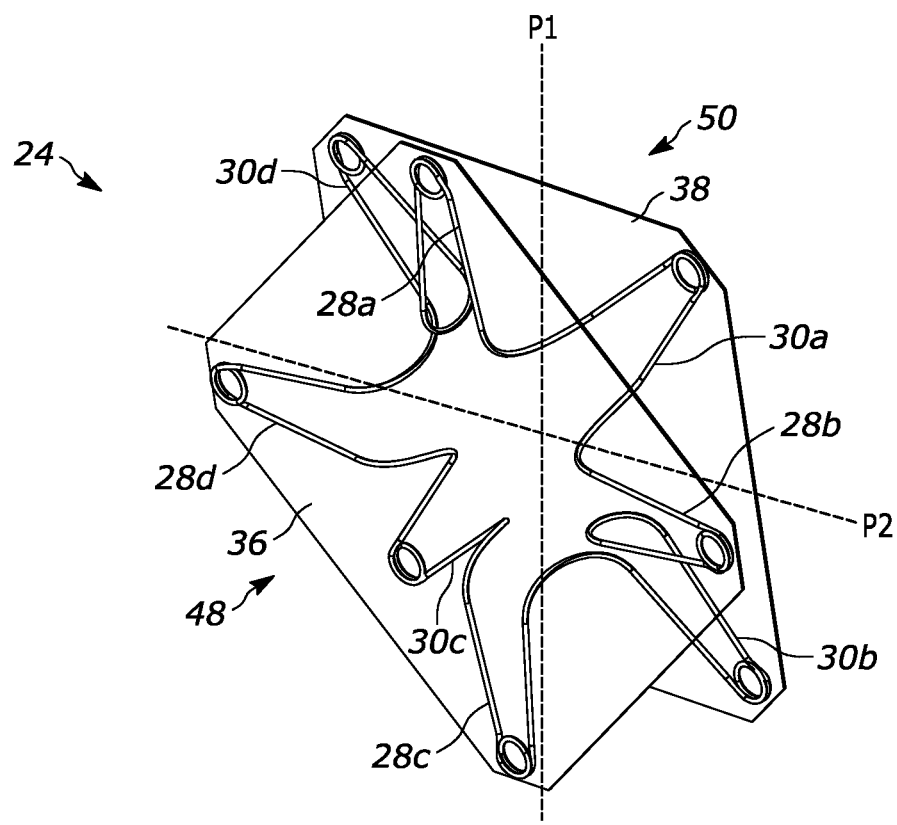
FIG. 5 is a perspective view of closure device according to an aspect of the present disclosure.

Referring to FIGS. 2-5, a closure device 24 is provided that comprises a continuous unitary frame 26. Frame 26 comprises a plurality of radially extendible distal fingers 28 extending in a distal plane P1 and a plurality of radially extendible proximal fingers 30 extending in a proximal plane P2. As can be seen be FIG. 5, plane P1 and plane P2 extend in different, non-parallel directions. Such a non-parallel alignment can result in greater compressive forces exerted by the plurality of fingers against the respective lateral faces of tissue defining the bodily opening to secure the device to the lateral faces of the tissue to sufficiently seal the bodily opening and inhibit the flow of liquids therethrough. Because the frame can be a continuous unitary structure, the plurality of proximal fingers and the plurality of distal fingers are not mechanically separate and are integrally connected or continuously attached. For example, the frame can comprise a one-piece single wire or tubular structure. In certain aspects, the plurality of distal fingers and the plurality of proximal fingers alternate such that a distal finger is immediately adjacent to a proximal finger and vice versa. In such an aspect, every other finger is a distal finger and the remaining fingers are proximal fingers. FIGS. 1 and 2 illustrate such an alternating pattern where distal finger 28a (for example) is immediately adjacent to proximal finger 30a (for example) because there are no intervening fingers between distal finger 28a and proximal finger 30a. In other words, for any given distal finger, such finger can be immediately adjacent to a proximal finger such that there are no intervening distal finger(s) between the given distal finger and the immediately adjacent proximal finger. Similarly, for any given proximal finger, such finger can be immediately adjacent to a distal finger such there are no intervening proximal finger(s) between the given proximal finger and the immediately adjacent distal finger. Such a configuration where this alternating pattern is repeated for all distal and proximal fingers is best illustrated in FIGS. 3 and 5. However, the number of distal fingers can be more than the number of proximal fingers and vice versa. As shown in FIG. 4, frame 26 includes a waist section 34 between the plurality of distal fingers 28 and the plurality of proximal fingers 30. The waist section 34 is defined by a plurality of vertices 32 between immediately adjacent fingers and is configured to be positioned within the bodily opening and can, for example, contact the walls of the tissue defining the bodily opening to sealingly engage the bodily opening.

Figure 19:
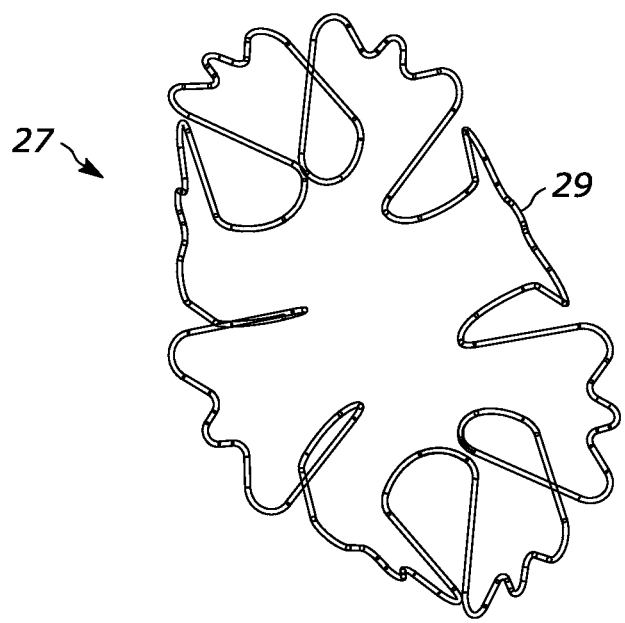
FIG. 19 is a perspective view of a frame of a closure device according to an aspect of the present disclosure.
Figure 20:
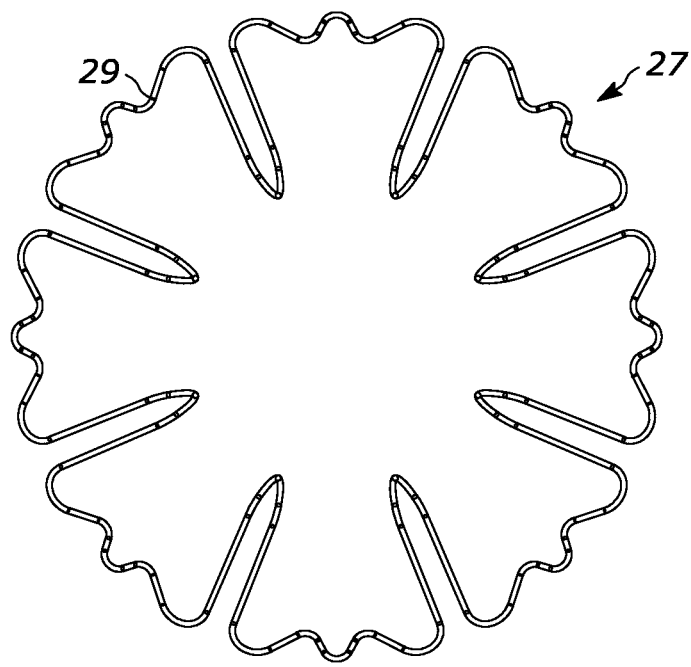
FIG. 20 is a top view of the frame of FIG. 19.
Figure 21:
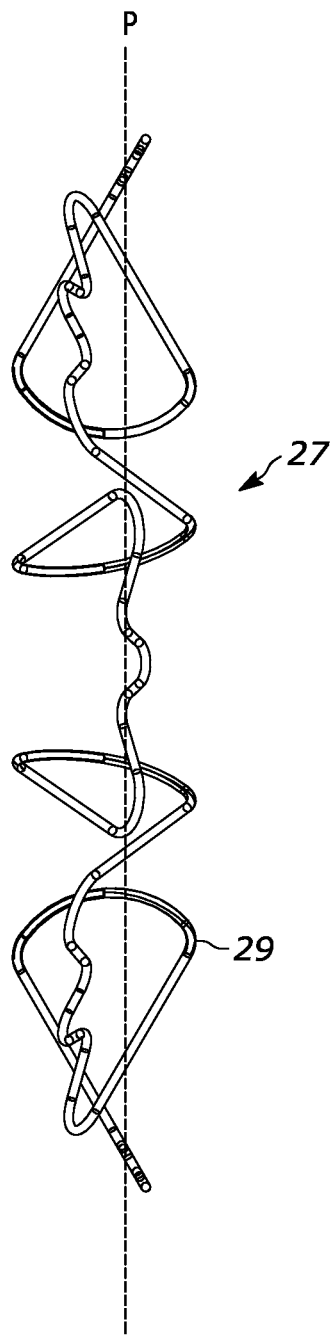
FIG. 21 is a side view of the frame of FIG. 19.

The device should be appropriately sized or oversized to the aperture of the defect. The size and shape of the plurality of fingers and the waist section can correspond with the size of the bodily opening and adjacent tissue and can vary depending on the location of the bodily opening. For example, the size and shape of the plurality of fingers can be such that they sealingly engage the lateral faces of the bodily opening to occlude the bodily opening and the size and shape of the waist section can be such that it can be positioned within the bodily opening. The shape and design of the fingers can also be such that they avoid any potential interaction or interference with surrounding bodily and/or medical structure such as, for example, the mitral valve, tricuspid valve and pulmonary veins. The plurality of distal fingers and the plurality of proximal fingers can each have an arcuate tip as best illustrated in FIGS. 2, 3 and 5. In certain aspects, each of the fingers are substantially the same size. In other aspects, one or more of the fingers can be different sizes. In either case, the shape of the fingers defines a shape that allows the fingers to engage the lateral tissue faces defining the bodily opening, such as the septum of the heart having an ASD, in a clasp or clamp-like manner. Referring to FIG. 19-21, in certain aspects, a closure device 27 has fingers 29 with a petal shape. Such petal shaped fingers can extend in different planes such that the frame's petals on one side would all sit radially along the surface of a shallow cone when deployed. In particular, fingers 29 from one side cross over an imaginary plane (depicted by reference character P in FIG. 21) in an unbound state acting similar to an unstretched/uncompressed spring. Once the crossing fingers are placed between the septum, for example, the fingers will deflect. This deflection from an unbound state provides a clamping force to keep the frame secured in place and maintains the membrane close to the septum's surface for less leakage. In other words, such "crisscrossing" of the fingers pre-loads the fingers to better clamp on the septum & pull in the sealing membrane to sit against the septal wall to minimize leakage.

As stated above, the frame can comprise a wire or tubular structure. The diameter or thickness of the wire or tubular structure can be generally proportional to the size of the closure device. For example, the diameter or thickness of the wire or tubular structure can be between about 50 μm and about 2000 μm. In other aspects, the diameter can be between about 200 μm and about 1000 μm. In other aspects, the diameter can be between about 200 μm and about 300 μm. In yet other aspects, the diameter can be approximately 300 μm.

As described in more detail below, the closure device is flexible and is configured to assume both radially collapsed configuration in which the frame is elongated axially and a radially expanded configuration in which the frame is shortened axially. The flexibility of the frame allows for the device to be expanded, contracted, and positionally adjusted to accommodate bodily openings and adjacent tissue of varying shapes and sizes. Further, the frame can be collapsible or capable of being distorted so that the device can be, among other things, deployed via transcatheter techniques. As such, the frame can be fabricated from a flexible and manipulatable materials (e.g. metals or polymers) such as, for example, iron, magnesium, platinum, stainless steel, cobalt-chromium-nickel allow or nickel titanium metal alloy (such as nitinol). In certain aspects, the frame is fabricated from a self-expanding shape memory material, such as nitinol for example, that can maintain the device's intended shape once it is released from a delivery device or otherwise deployed. The frame can also include biodegradable materials, PLA, PLLA, other magnesium-based materials, or suitable combinations thereof. The frame can be fabricated by laser cutting a flat sheet of a flexible material such as nitinol or by forming the frame from a flexible material.

Figure 22:
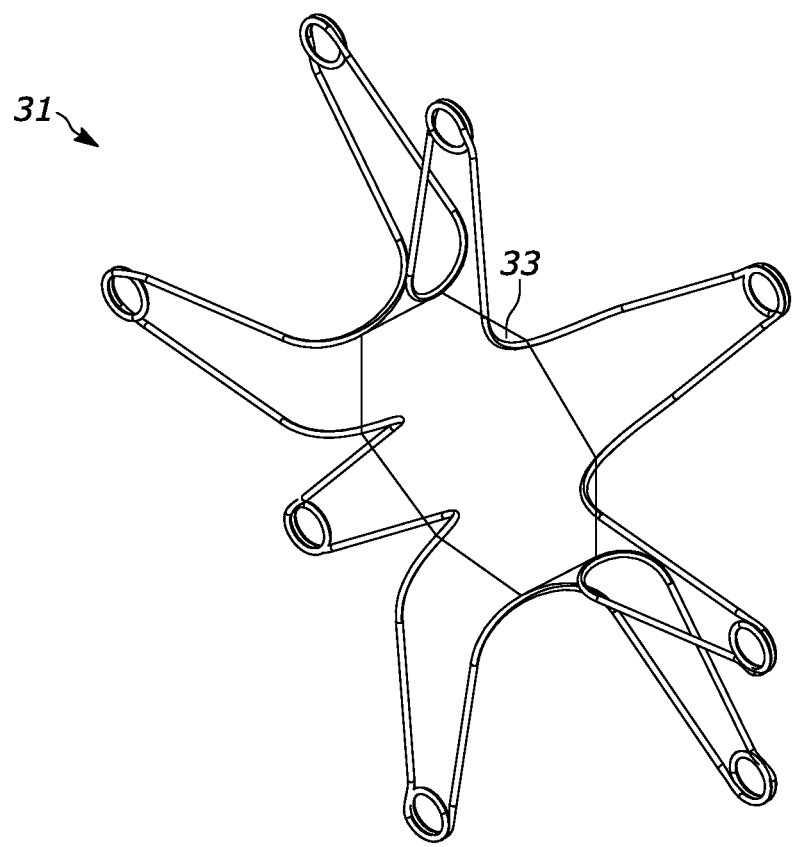
FIG. 22 is a perspective view of a frame of a closure device according to an aspect of the present disclosure.
Figure 23:
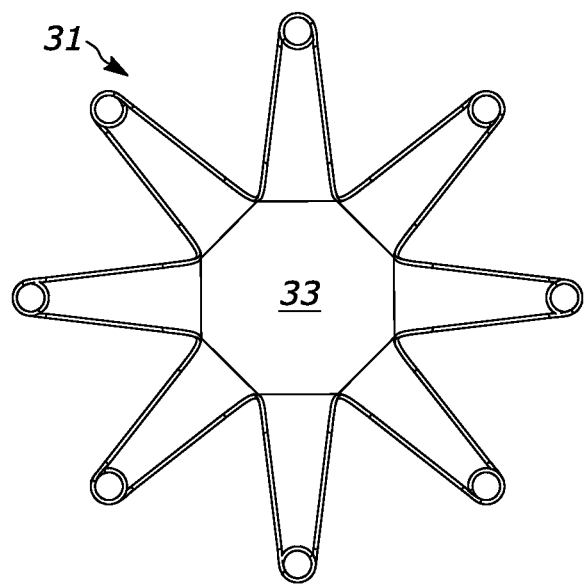
FIG. 23 is a top view of the frame of FIG. 22.
Figure 24:
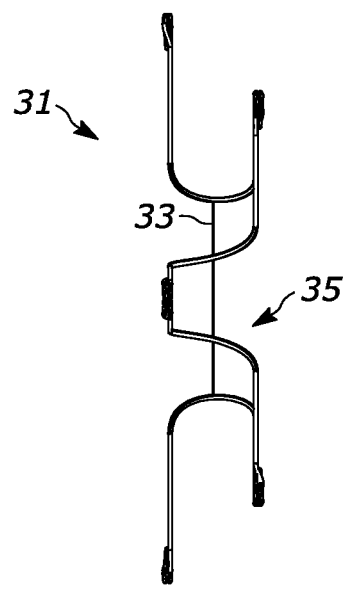
FIG. 24 is a side view of the frame of FIG. 22.
Figure 25:
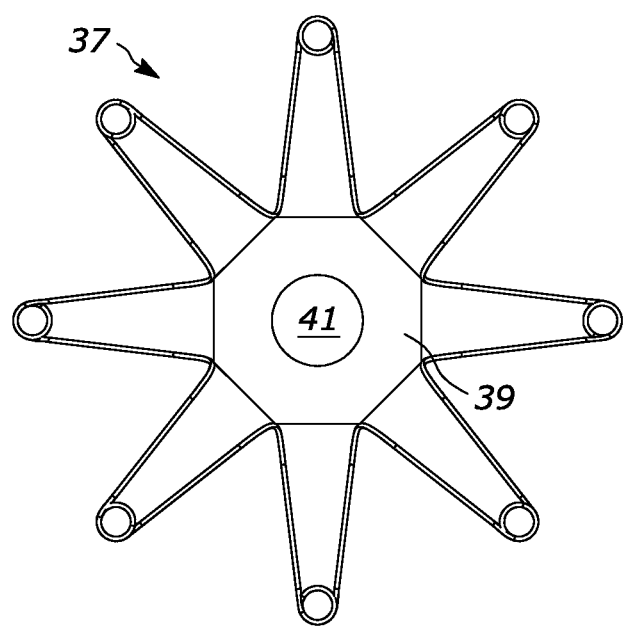
FIG. 25 is a top view of a closure device according to an aspect of the present disclosure.
Figure 26:
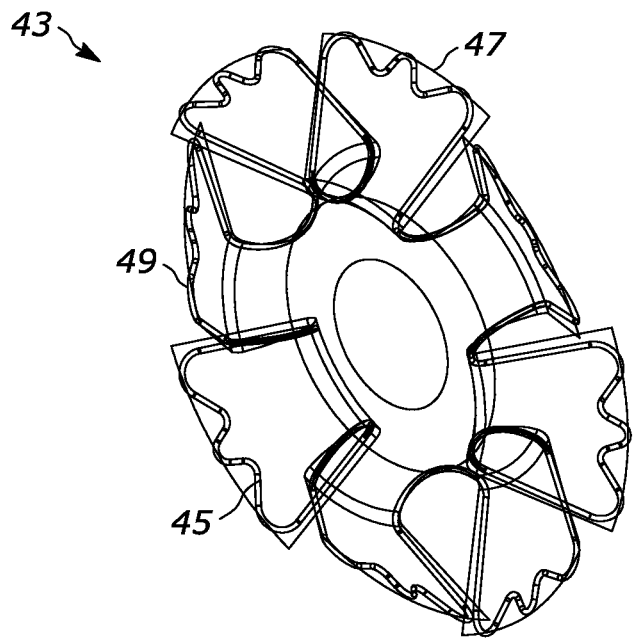
FIG. 26 is a perspective view of a closure device according to an aspect of the present disclosure.
Figure 27:
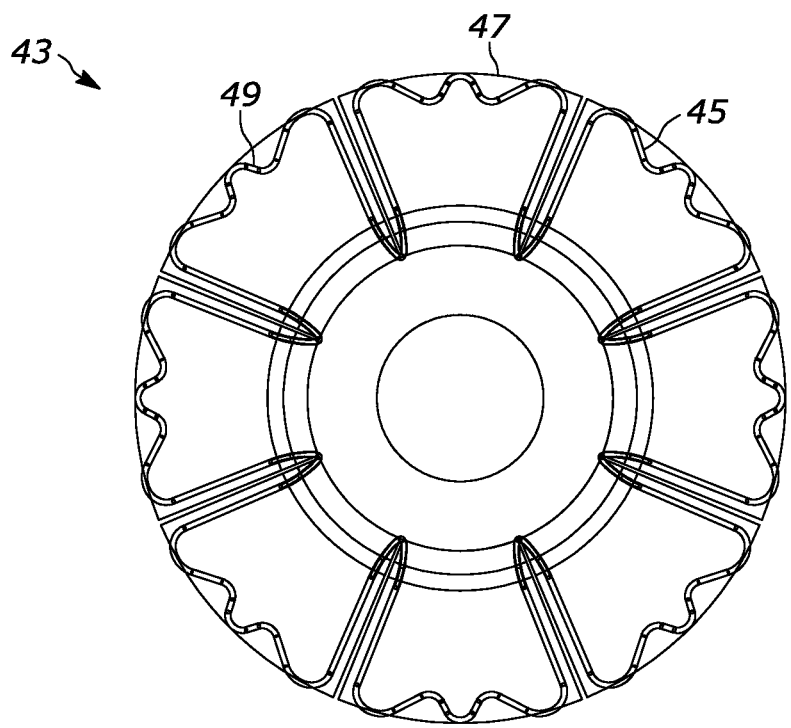
FIG. 27 is a top view of the closure device of FIG. 26.
Figure 28:
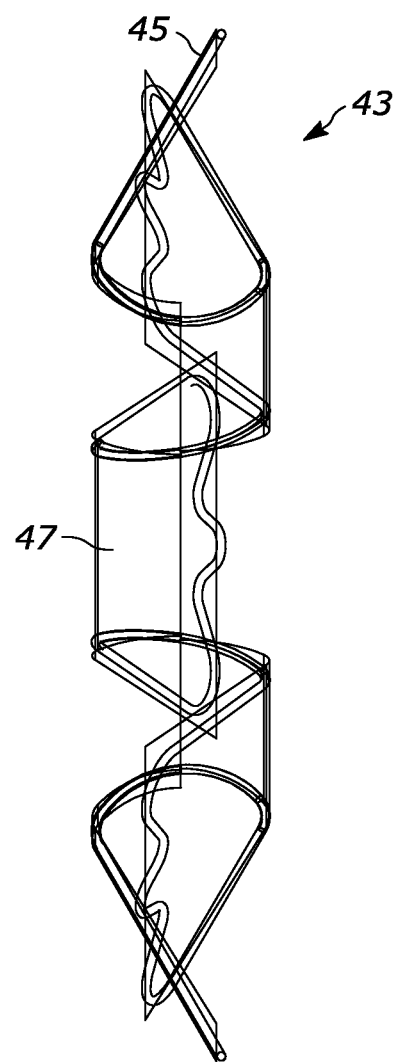
FIG. 28 is a side view of the closure device of FIG. 26.

Referring to FIG. 5, in an embodiment, closure device 24 further includes a distal membrane 36 covering at least one side of the plurality of distal fingers 28 (collectively referred to as the "distal closure portion 48") and a proximal membrane 38 covering at least one side of the plurality of proximal fingers 30 (collectively referred to as the proximal closure portion 50"). Alternatively, referring to FIG. 22-24, a closure device 31 can include a single membrane 33 that covers expandable waist section 35. The membranes are adapted to sealingly engage lateral tissue faces defining the bodily opening that is to be sealed. The plurality of fingers can hold the respective membrane substantially taut. Referring to FIGS. 25-27, in certain aspects, a closure device is provided that includes an aperture within the membrane to alleviate too high of pressure in one atrium. Such an aperture can shunt the blood to the other atrium, which is at a lower pressure. FIG. 25 illustrates a closure device 37 where the aperture 41 is located within membrane 39. FIGS. 26-28 illustrate a closure device 43 with a sealing membrane 47 covering frame 45. Fingers 49 of closure device 43 have a broader petal shape with an alternating & more secure attachment of membrane 47 to the frame.

Figure 10:
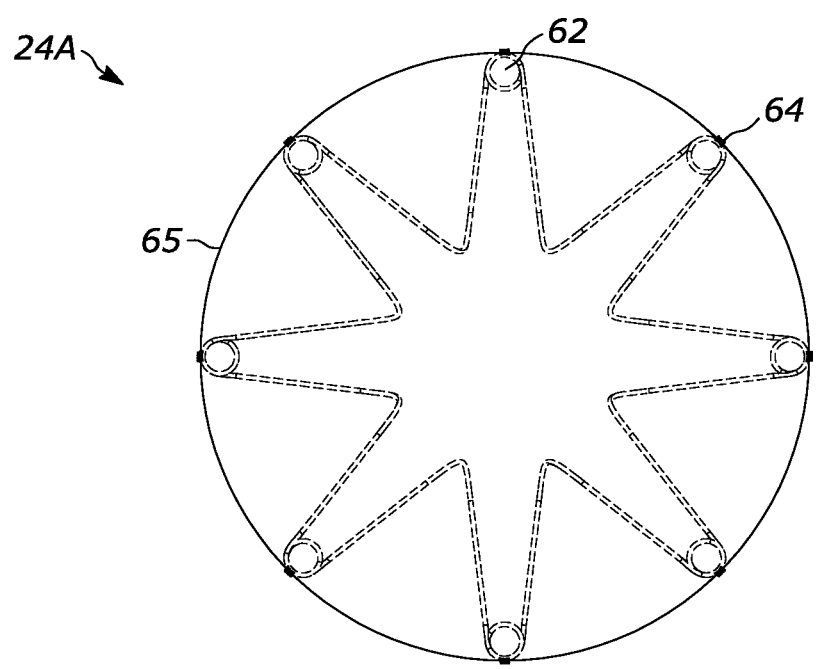
FIG. 10 is a schematic illustration of a distal and/or proximal membrane of a closure device according to an aspect of the present disclosure.

The membranes can be fabricated from a material that is sufficiently resilient and flexible and is sufficiently durable to allow post-deployment medical punctures without jeopardizing the integrity of the membranes. For example, the membranes can be fabricated from an expanded polytetrafluoroethylene or a bioremodelable material, such as polytetrafluoroethylene (PTFE); expanded polytetrafluoroethylene (ePTFE); a fabric such as a polyester fabric; Teflon-based materials; pericardium tissue; other biocompatible or bioabsorbable materials; or suitable combinations thereof. In certain aspects, the membrane can comprise a silk, nylon, silicone, polyethylene, polypropylene, or fluoropolymer membrane. However, the membrane preferably comprises a biocompatible material that does not produce a significant inflammatory response or calcification response, including a PTFE, ePTFE, polyethylene terephthalate (PET), or other polyethylene membrane, pericardium, or other polymer. Preferably, the membrane is fabricated from a material that inhibits the passage of blood while also permitting post-deployment transseptal punctures and interatrial re-entry. The membrane can be a PET mesh, a PTFE laminate baked by PET (discussed below) or other suitable materials. The membranes can be attached to the respectively plurality of fingers by sutures or other suitable attachment devices and methods such as an adhesive, gluing, heat sealing, through the use of electricity, polymerization, welding or the like. The plurality of proximal fingers and the plurality of distal fingers can each comprise an attachment point for the respective proximal membrane and distal membrane. For example, the attachment point be an eyelet 62 sized to receive a suture(s). The eyelets can be located at the distal end of the fingers. As illustrated in FIG. 10, suture knots 64 can be tied to the eyelets. The eyelets can provide robust anchoring of the membrane 65 to the frame as the suture(s) will not slide out of place on the frame.

Figure 9:
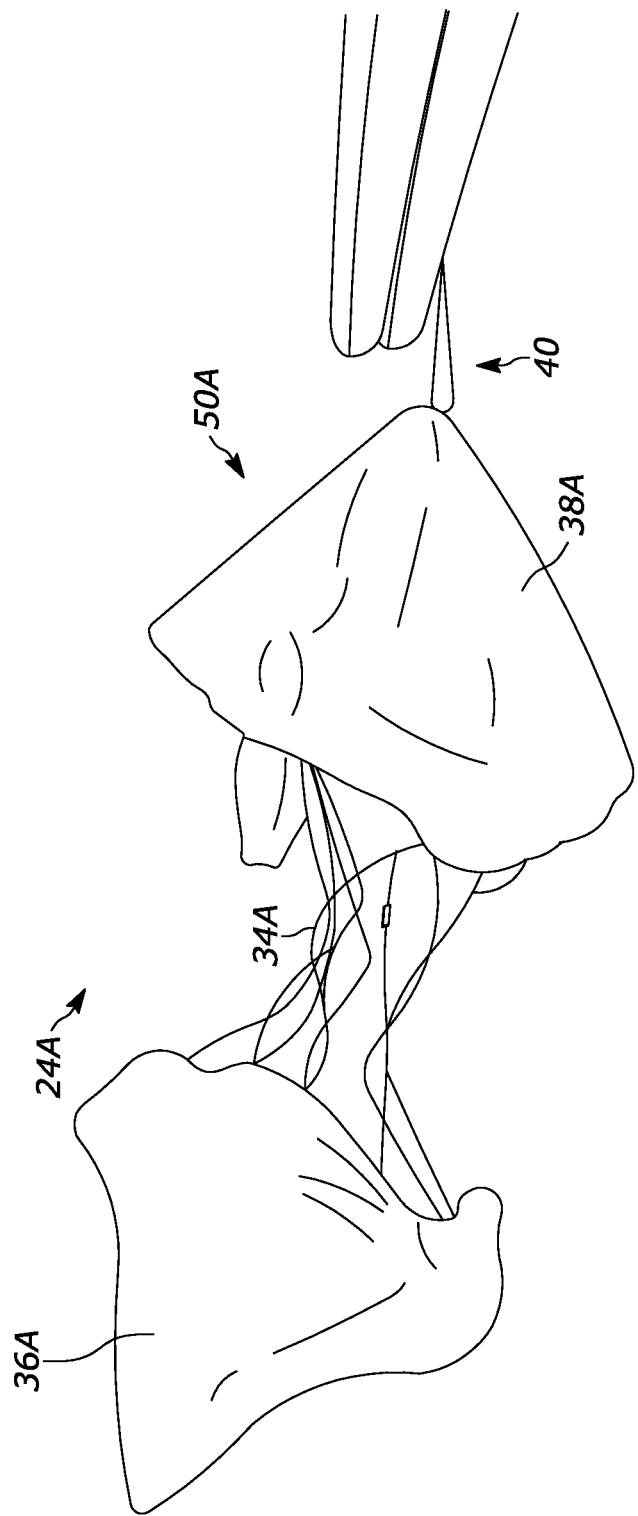
FIG. 9 is a schematic illustration of a closure device in an elongated position prior to loading into a delivery device according to an aspect of the present disclosure.

A thread, cable or other resistant elongated material 40, illustrated in FIG. 9, can be attached to the proximal membrane 38A (but could also be attached the distal membrane 36A). The thread can be, for example, a polymeric fiber or a wire. The thread can be attached to the center of the proximal membrane or the distal membrane. As described in detail below, the thread can facilitate the release or deployment of the device and can be used to pull the device into a delivery device prior to the delivery or deployment of the device. As stated above, the suture knots can be attached to the eyelets of the frame, which can be located at the distal end of the fingers. By attaching the sutures (and thus the membrane(s)) only at the distal end of the fingers, when the thread is pulled proximally from the center of the proximal membrane or the distal membrane, the membrane is allowed to pivot away from the frame. This may not be possible if the membrane were attached at other portions of the frame. This can be advantageous because it allows the closure device to load into a delivery catheter having a smaller diameter. The smaller the delivery catheter diameter is, the easier the procedure can be on the patient and a larger patient population can be treated.

Figure 11:
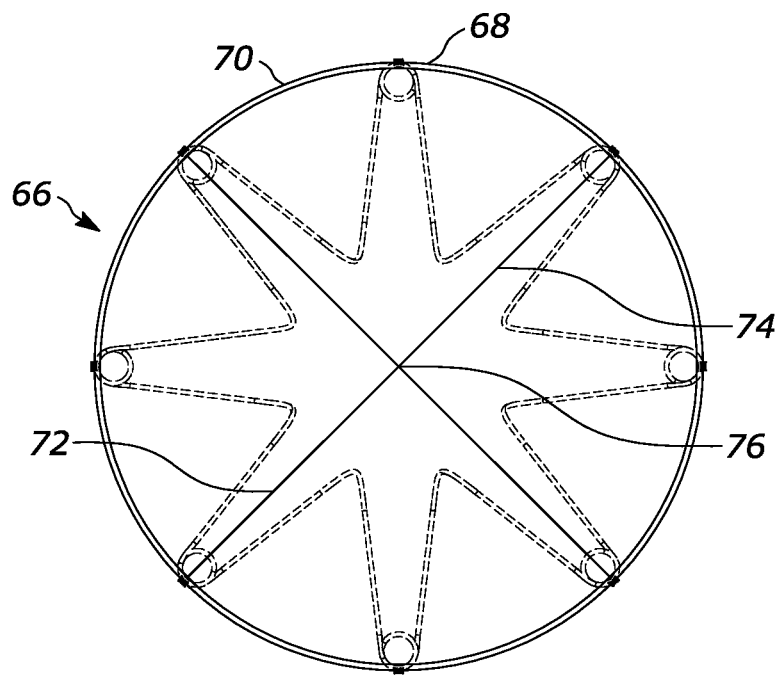
FIG. 11 is a schematic illustration of the distal and/or proximal membrane of FIG. 10 with a pulling thread attached to the membrane.
Figure 12:
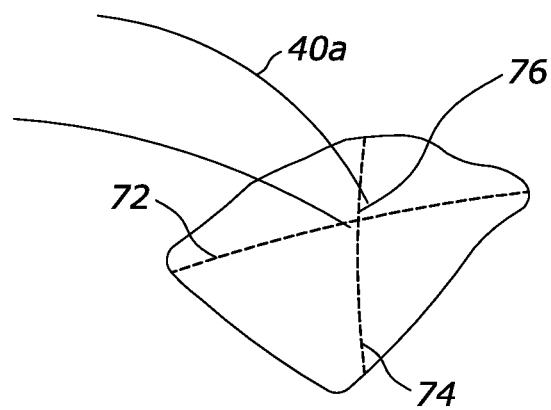
FIG. 12 is a schematic illustration illustrating a side view of the closure device of FIG. 9.

Referring to FIGS. 11 and 12, in certain aspects, a distal membrane/proximal membrane 66 comprises a first sheet 68 comprising an outer surface comprising a fluoropolymer and an inner surface comprising a thermoplastic polymer. The membrane(s) can further comprise a second sheet 70 comprising an outer surface comprising a fluoropolymer and an inner surface comprising a thermoplastic polymer. The fluoropolymer can be polytetrafluoroethylene (PTFE) or any other suitable fluoropolymer and the thermoplastic polymer can be polyethylene terephthalate (PET) or any other suitable thermoplastic polymer. The inner surface of the second sheet can be laminated to the inner surface of first sheet (FIG. 11 depicts a space between the two sheets for purposes of clarity but such a space need not exist when the two sheets are laminated together. Further, sheet 70 is depicted with a solid line for purposes of clarity). First and second reinforcing filaments 72 and 74 can be disposed between first sheet 68 and 70 and can criss-cross at an intersection point 76. First reinforcing filament 72 can have ends 78a and 78b attached to frame 80 and second reinforcing filament 74 can have ends 82a and 82b attached to frame 80. In particular, the first and second filaments 72 and 74 can anchor first and second sheets 68 and 70 to frame 80 and can carry the loading and retrieval loads of membrane 66. As seen in FIG. 11, ends of the reinforcing filaments can be tied to the frame's eyelets to provide requisite anchoring knots. As shown in FIG. 12, thread 40A can be attached to the first and second reinforcing filaments at intersection point 76. When thread 40A is looped through at intersection point 76, thread 40A can be pulled proximally transferring the loading forces into the criss-crossed filaments without loading and deforming the soft fluoropolymer of the first and second sheets.

Figure 13:
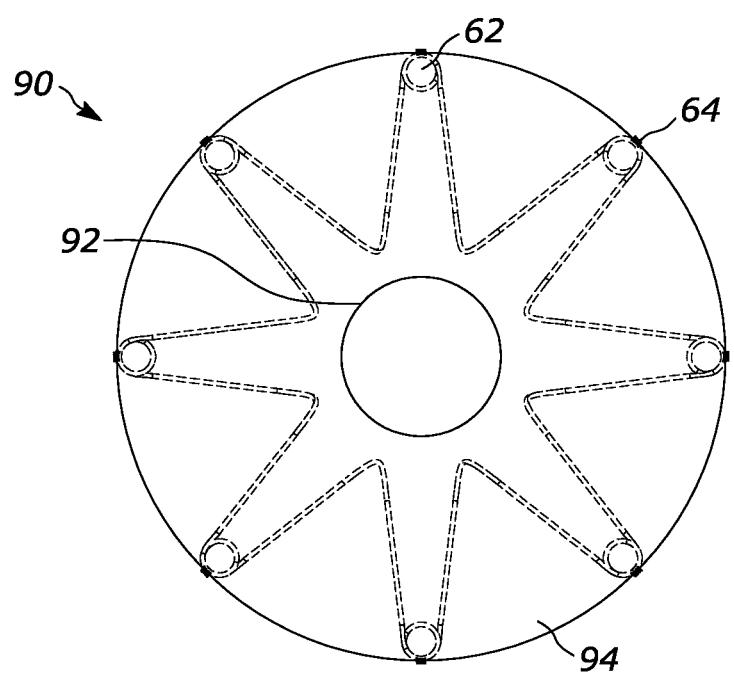
FIG. 13 is a schematic view of the closure device of FIG. 9 loaded into a catheter.

Referring to FIG. 13, in certain aspects a closure device 90 comprises a reinforcing material 92 attached to the proximal membrane or the distal membrane 94. A thread as described above can be attached to (e.g. looped through) the center of reinforcing material 92. As described above, the thread can facilitate the release or deployment of the device and can be used to pull the device into a delivery device prior to the delivery or deployment of the device.

The closure device is configured to transition from a series of shapes. For example, in a radially collapsed configuration the frame is elongated axially. Such an elongated shape can allow the closure device to be loaded into a delivery device so that it can be delivered percutaneously to the target site. When transitioning to the radially expanded configuration, the frame is shortened axially. In such a radially expanded configuration, the waist section is positioned in the bodily opening, the plurality of distal fingers engages one side of the tissue wall defining the bodily opening, and the plurality of proximal fingers engages the other side of the tissue wall defining the bodily opening such that the distal and proximal membranes are pressed against the sides of the tissue wall to seal the bodily opening. In a radially expanded configuration, the distal and proximal planes can be maintained in a specified spaced relationship, including for example, an axially spaced relationship. In certain aspects, the closure device is configured so that it is biased to assume its intended shape while in the radially expanded configuration when the device is free from any restraining forces caused by the delivery device or the like.

Figure 6:
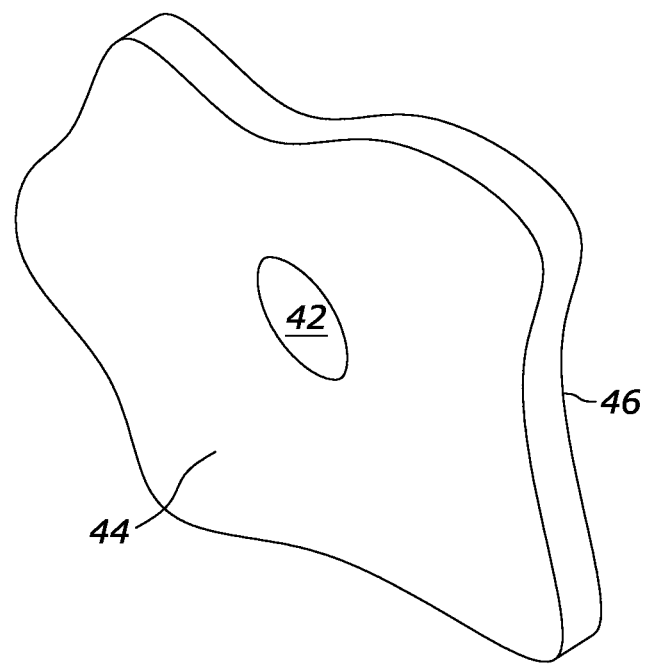
FIG. 6 is a schematic illustration of a cardiac septum including an ASD.
Figure 7:
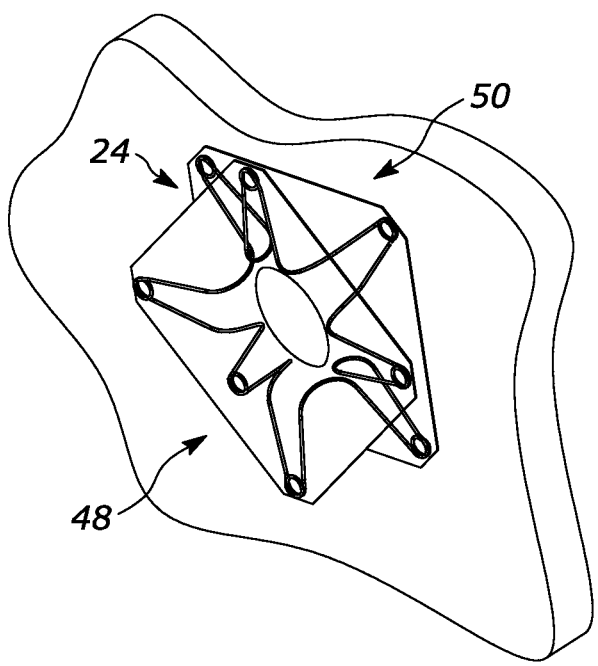
FIG. 7 is a schematic illustration of a closure device placed against the cardiac septum of FIG. 6.
Figure 8:
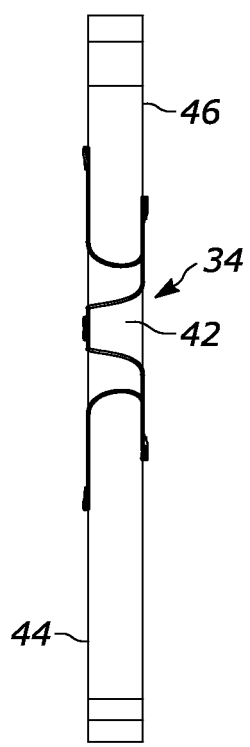
FIG. 8 is a side view of FIG. 7.

In certain aspects, the closure device is used to treat an ASD. FIG. 6 illustrates an ASD 42 between a left septal wall 44 and a right septal wall 46. FIG. 7 illustrates closure device 24 in a deployed position where the distal closure portion 48 sealingly engages left septal wall 44 and proximal closure portion 50 sealingly engages right septal wall 46. Of course, it is understood that depending on the direction of entry, distal closure portion 48 can sealingly engage right septal wall 46 and proximal closure portion 50 can sealingly engage left septal wall 46. The alternating pattern of the distal and proximal fingers can facilitate the fingers gripping the septum across the ASD to hold the closure device in place. Such a clamping action can also hold the membranes of the closure device against the respective sides of the cardiac septum. The alternating pattern also minimizes the amount of metal or other fabrication material that could interfere with a potential subsequent procedure that would require puncturing through the closure device. As illustrated in FIG. 8, waist section 34 is positioned within ASD 42. The waist section of the closure device functions to self-center the device in the ASD, which in turn centers the proximal and distal membranes over the ASD to provide sufficient sealing of the ASD.

Figure 14:
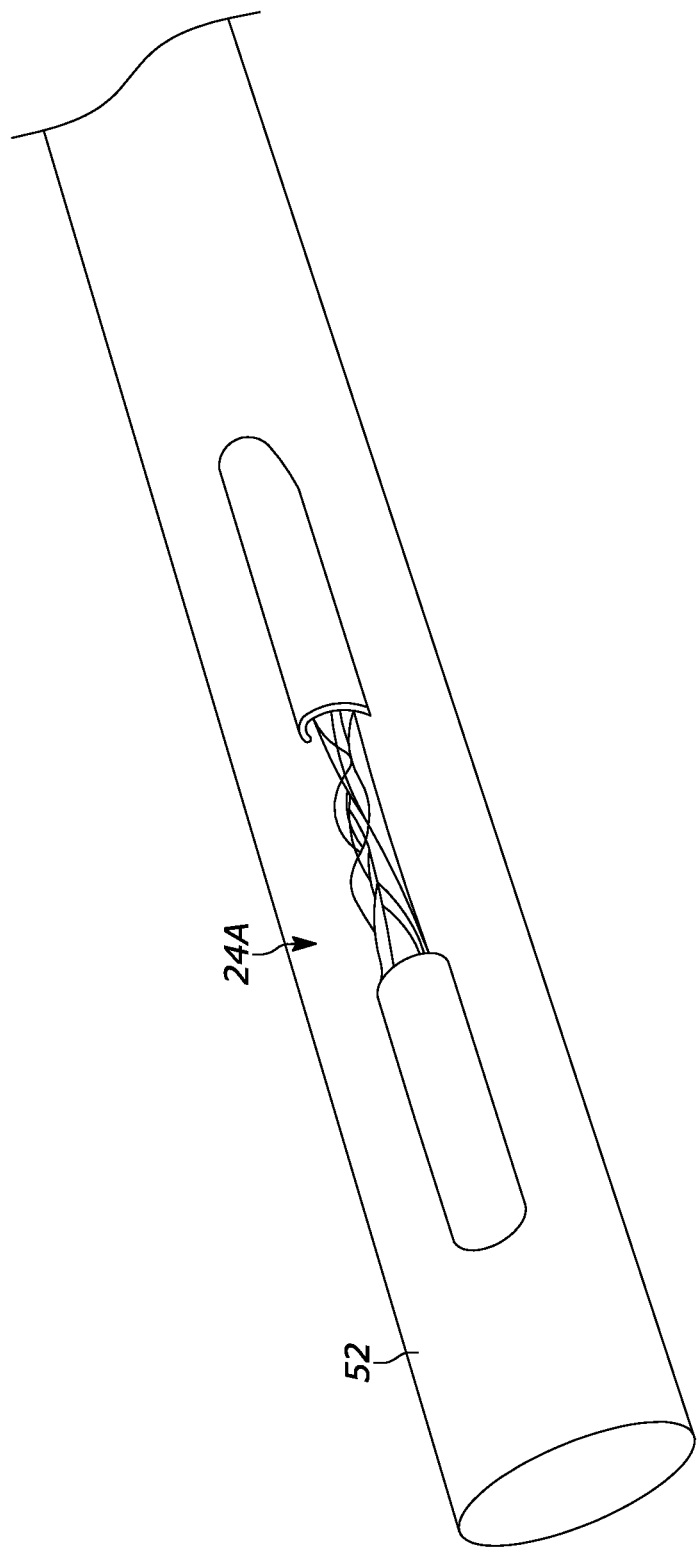
FIG. 14 is a schematic illustration of the closure device of FIG. 9 prior to insertion into a ASD of a cardiac septum with the cardiac septum represented by a silicone sheet and the aperture in the silicone sheet representing the ASD.
Figure 15:
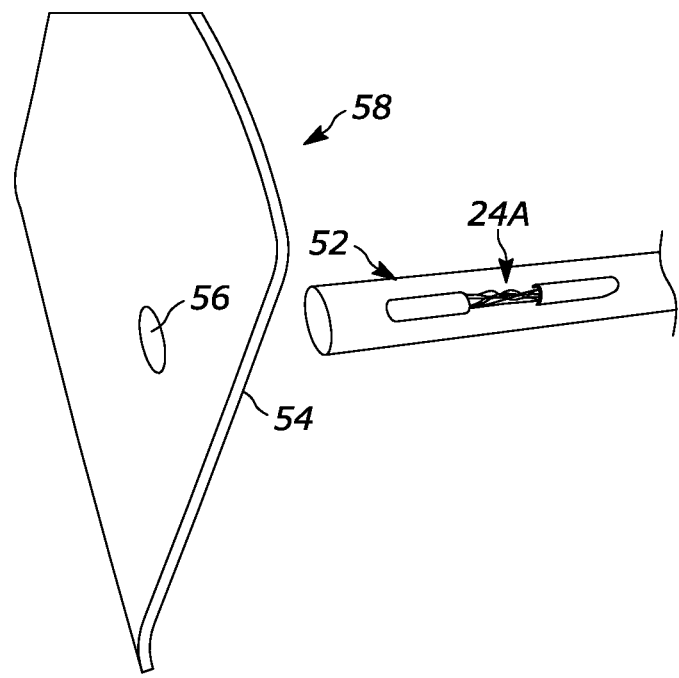
FIG. 15 is a schematic illustration of the closure device of FIG. 9 inserted through the ASD.
Figure 16:
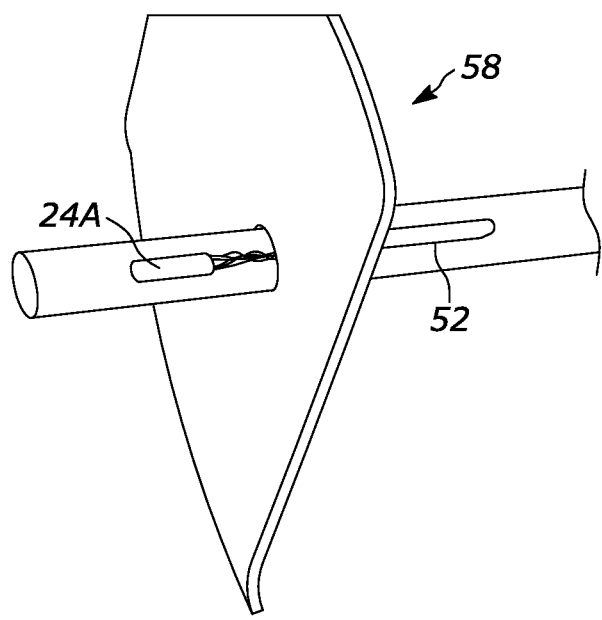
FIG. 16 is a schematic illustration of a distal closure portion of the closure device of FIG. 9 deployed on the left side of the cardiac septum.
Figure 17:
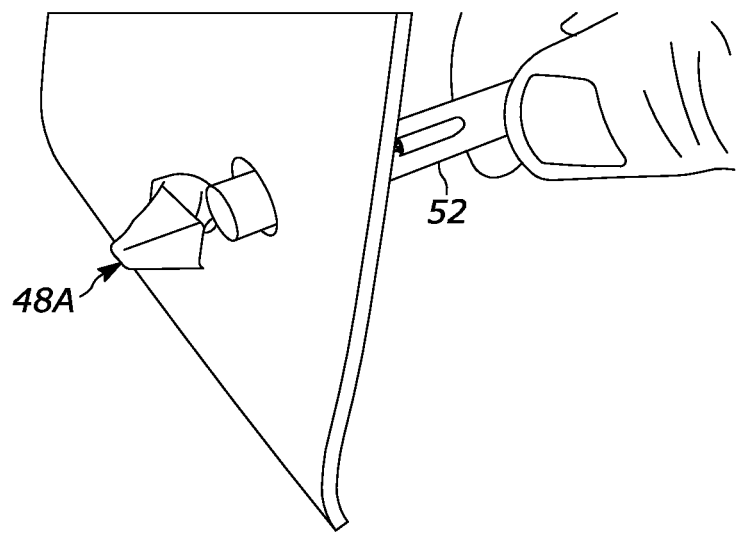
FIG. 17 is a schematic illustration of the proximal portion of the closure device of FIG. 9 deployed and positioned against the right side of the cardiac septum.
Figure 18:
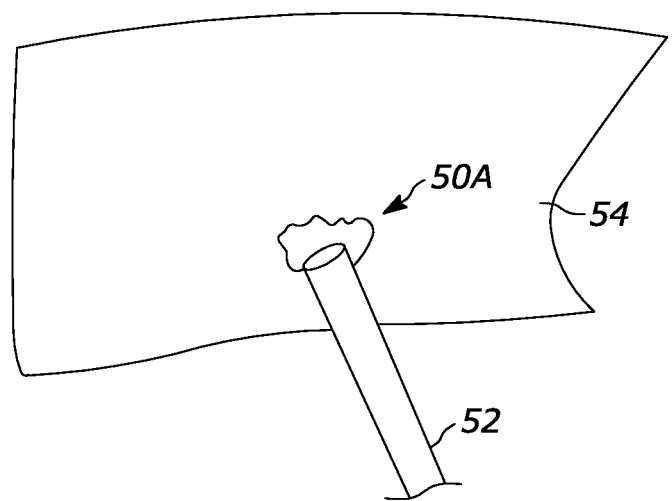
FIG. 18 is a schematic illustration of the closure device of FIG. 9 in a fully deployed position

FIGS. 9 and 14-19 provide a schematic depiction of a method of using closure device 24A. FIG. 9 illustrates closure device 24A in a radially collapsed configuration where the frame is elongated axially. To transition closure device 24A into a radially expanded configuration, thread 40, which is shown looped through the center of membrane 38A of proximal closure portion 50A, can be pulled in a proximal direction. To load closure device 24A into a delivery device, thread 40 can be pulled through the distal end of the delivery device. By drawing membrane 38A in at the center, the closure device has the capability to be retrieved and reloaded into the delivery device if necessary. FIG. 14 illustrates closure device 24A loaded into a catheter 52. It should be noted that catheter 52 is shown as being clear in order to better illustrate the components loaded in catheter 52. FIG. 15 illustrates catheter 52 being positioned towards a right cardiac septal wall 54. FIG. 16 illustrates catheter 52 being guided through the ASD 56 of the cardiac septum 58. Catheter 52 can be retracted to deploy the distal closure portion 48A as illustrated in FIG. 17. Catheter 52 can then be further retracted so that proximal closure portion 50A is on the right cardiac septal wall 54 as illustrated in FIG. 18. The device is now fully deployed with the distal closure portion 48A sealingly engaging the left septal wall 60 and proximal closure portion 50A sealingly engaging the right septal wall. Again, depending on the direction of entry, the position of the distal closure portion and the proximal closure portion can be reversed. Prior to full release, the closure device can be repositioned or retrieved. In a fully deployed and implanted configuration, the device straddles across the septum and the waist section of the closure device is positioned and centered in the ASD. The proximal and distal closure portions can be placed on top of each other and still seal allowing for resealing the opening if necessary.

Although the above-referenced description refers primarily to ASDs, the closure device can be used to occlude other opening in bodily tissue, such as patent foramen ovales (PFO); other arterio-venuous communications; patent ductus arteriosus; and other man-made, congenital, or acquired openings (such as openings acquired by disease for example) in a minimally invasive manner. Further, the device can be configured to be used with adult and/or child patients.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure.

What is claimed is:

1. A device for closing an opening in a tissue wall comprising:
    a continuous unitary frame comprising:
        a plurality of radially extendible distal fingers extending in a distal plane;
        a plurality of radially extendible proximal fingers extending in a proximal plane, the proximal plane being different from and non-parallel with the distal plane;
        an expandable waist section extending axially between the plurality of radially extendible distal fingers and the plurality of radially extendible proximal fingers;
    a distal membrane covering at least one side of the plurality of radially extendible distal fingers;
    a proximal membrane covering at least one side of the plurality of radially extendible proximal fingers;
    first and second reinforcing filaments criss-crossing at a central intersection point and having ends attached to at least opposing ones of the plurality of radially extendible proximal fingers, the plurality of radially extendible distal fingers, or both;
    wherein the device is expandable from a radially collapsed configuration in which the continuous unitary frame is elongated axially to a radially expanded configuration in which the continuous unitary frame is shortened axially; and
    wherein in the radially expanded configuration, the expandable waist section is configured to be positioned within the opening in the tissue wall, the plurality of radially extendible distal fingers is configured to engage one side of the tissue wall defining the opening, and the plurality of radially extendible proximal fingers is configured to engage the other side of the tissue wall defining the opening such that the distal and proximal membranes are pressed against the sides of the tissue wall to seal the opening.

2. The device of claim 1, wherein the plurality of radially extendible distal fingers and the plurality of radially extendible proximal fingers alternate such that a distal finger is immediately adjacent to a proximal finger.

3. The device of claim 1, further comprising a thread attached to the proximal membrane or the distal membrane, the thread configured to be pulled to load, retrieve and/or re-load the device into a delivery device.

4. The device of claim 3, wherein the thread is attached to the center of the proximal membrane or the distal membrane.

5. The device of claim 3, further comprising a reinforcing material adhered to the proximal membrane or the distal membrane, the thread attached to the reinforcing material.

6. The device of claim 3, wherein the thread is attached to the first and second reinforcing filaments at the intersection point.

7. The device of claim 1, wherein the plurality of radially extendible proximal fingers and the plurality of radially extendible distal fingers each comprise an attachment point for the respective proximal membrane and distal membrane, the attachment point comprising an eyelet sized to receive a suture.

8. The device of claim 7, further comprising suture knots tied to the eyelets.

9. The device of claim 1, wherein the continuous unitary frame is fabricated from a shape memory material.

10. The device of claim 1, wherein the plurality of radially extendible distal fingers and distal membrane are sized and shaped to sealingly engage one of the left or right side of a septal wall, the plurality of radially extendible proximal fingers and proximal membrane are sized and shaped to sealingly engage the other of the left or right side of the septal wall, and the expandable waist section is sized and shaped to be positioned and centered in an atrial septal defect between the left and the right septal wall.

11. The device of claim 1, wherein the proximal membrane, the distal membrane, or both are repuncturable.

12. The device of claim 1, wherein at least a portion of the device is bioresorbable.

13. The device of claim 1, wherein at least some of the plurality of radially extendible proximal fingers, the plurality of radially extendible distal fingers, or both have a petal shape.

14. The device of claim 1, wherein the proximal membrane and the distal membrane each define an opening extending therethrough.

* * * * *